United States Patent [19]  [11]  4,191,711
Lenthe et al.  [45]  Mar. 4, 1980

[54] PROCESS FOR THE PREPARATION OF CERTAIN NUCLEAR CHLORINATED BENZOTRICHLORIDES

[75] Inventors: Manfred Lenthe, Lohmar; Hans-Helmut Schwarz, Krefeld, both of Fed. Rep. of Germany

[73] Assignee: Bayer Aktiengesellschaft, Leverkusen, Fed. Rep. of Germany

[21] Appl. No.: 925,494

[22] Filed: Jul. 17, 1978

Related U.S. Application Data

[63] Continuation of Ser. No. 832,758, Sep. 12, 1977, abandoned.

[30] Foreign Application Priority Data

Oct. 2, 1976 [DE] Fed. Rep. of Germany ....... 2644641

[51] Int. Cl.$^2$ ..................... C07C 25/08; C07C 25/16
[52] U.S. Cl. ........................... 260/650 R; 260/651 R
[58] Field of Search ..................... 260/650 R, 651 R

[56] References Cited

U.S. PATENT DOCUMENTS 2,608,591  8/1952  Lawler ........................... 260/650 R
2,956,084  10/1960  Enz et al. ....................... 260/651 R
3,219,688  11/1965  Weil et al. ...................... 260/651 R Primary Examiner—C. Davis
Attorney, Agent, or Firm—Sprung, Felfe, Horn, Lynch & Kramer

[57] ABSTRACT

A process for the preparation of 3,4-dichlorobenzotrichloride, 3,4,5-trichlorobenzotrichloride, 2,4,5-trichlorobenzotrichloride or 2,3,4,5-tetrachlorobenzotrichloride which comprises contacting p-chlorobenzotrichloride of the formula

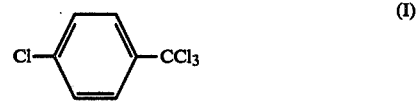

(I)

with chlorine or an agent which releases chlorine at a temperature between 0° C. and 180° C. in the presence of an iron (III) chloride or aluminum chloride catalyst or a mixture of iron (III) chloride or aluminum chloride with sulfur dichloride or disulfur dichloride.

14 Claims, No Drawings

PROCESS FOR THE PREPARATION OF CERTAIN NUCLEAR CHLORINATED BENZOTRICHLORIDES

This is a continuation of application Ser. No. 832,758, filed Sept. 12, 1977, and now abandoned.

BACKGROUND OF THE INVENTION

1. Field Of The Invention

The present invention relates to an unobvious process for the preparation of certain known benzotrichlorides chlorinated in the benzene ring which can be used, inter alia, as starting materials for the synthesis of herbicidally active compounds.

2. Discussion Of The Prior Art

The preparation of nuclear-chlorinated aromatic compounds by the reaction of aromatic substances with chlorine is one of the most frequently carried out reactions in organic chemistry. In general, mixtures of various highly chlorinated products and/or of position isomers are thereby obtained, from which pure compounds can be isolated only with a relatively high expenditure of work and in relatively low yields. However, methods which make the controlled syntheses of particular nuclear-chlorinated aromatic compounds possible have also been described in the literature.

Thus, several processes for the selective preparation of nuclear-chlorinated benzotrichlorides have already been disclosed (see U.S. Pat. Nos. 2,608,532, 2,608,591 and 3,297,771, British Patent Specification 771,416 and German Auslegeschrift (German Published Specification) 1,269,115). The disadvantage of these processes is, however, that the pure reaction products are not always obtained in sufficiently high yields. Furthermore, expensive process steps are frequently necessary, or the required starting materials are not accessible in a simple manner.

3,4-Dichlorobenzotrichloride can be synthesised, for example, by treating 1,4-bis-(trichloromethyl)-2-chlorobenzene with chlorine for about 8 hours at temperatures between 240° C. and 250° C. (see British Patent Specification 771,416). Although the desired product is obtained in good yield by this procedure, the industrial application of this process is hindered by several factors. Thus, the energy required for this reaction is quite considerable because very high reaction temperatures must be maintained over a relatively long period. Moreover, the compound employed as the starting material can be prepared only by a synthesis involving several stages.

It is also known that 2,4,5-trichlorobenzotrichloride can be prepared completely analogously to the above-mentioned synthesis of 3,4-dichlorobenzotrichloride by the action of chlorine on 1,4-bis-(trichloromethyl)-2,5-dichlorobenzene for several hours at temperatures of about 250° C. (see British Patent Specification 771,416). However, this process also has the disadvantages already mentioned.

Furthermore, it has been disclosed that 2,4,5-trichlorobenzotrichloride is also formed in the photochlorination of 2,4,5-trichlorotoluene with liquid chlorine at low temperatures (see U.S. Pat. No. 2,608,532). However, the yield of pure product in this procedure leaves much to be desired. In addition, the reaction must be carried out under pressure and the preparation of the isomer-free starting product involves some expense.

Furthermore, it is known that 2,3,4,5-tetrachlorobenzotrichloride can be synthesised by reacting 1,2,3,4-tetrachlorobenzene with carbon tetrachloride in the presence of aluminum chloride (see U.S. Pat. No. 3,297,771). However, in this procedure the compound is obtained only in a very low yield. Quite apart from this, the preparation of the starting material in a pure condition is relatively troublesome.

SUMMARY OF THE INVENTION

The present invention now provides a process for the preparation of 3,4-dichlorobenzotrichloride, 3,4,5-trichlorobenzotrichloride, 2,4,5-trichlorobenzotrichloride or 2,3,4,5-tetrachlorobenzotrichloride, in which p-chlorobenzotrichloride, which has the formula

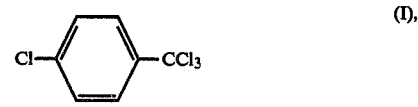

(I), is reacted, at a temperature between 0° C. and 180° C., with chlorine or with an agent which releases chlorine, in the presence of iron(III) chloride or aluminum chloride or a mixture of iron(III) chloride or aluminum chloride with sulphur dichloride or disulphur dichloride as a catalyst, optionally in the presence of an inert diluent.

It is surprising that the reaction according to the invention leads, with high selectivity, to particular nuclear-chlorinated benzotrichlorides since, with regard to the known state of the art, it had to be expected that a complex mixture of substances would be formed under the conditions used.

The process according to the invention has a number of advantages. Thus, it makes it possible to prepare particular nuclear-chlorinated benzotrichlorides in very good yield and excellent purity. Furthermore, it is to be pointed out that the course of the reaction can be influenced, by a slight variation in the reaction conditions, such as the reaction time and reaction temperature, in such a way that either 3,4-dichlorobenzotrichloride or 3,4,5-trichlorobenzotrichloride and 2,4,5-trichlorobenzotrichloride or 2,3,4,5-tetrachlorobenzotrichloride are formed with high selectivity. In addition, the chemicals required for the reaction are also accessible on an industrial scale in a simple manner. Furthermore, the working up (recovery) of the reaction products obtained after the reaction has ended presents no difficulties since the reaction products can be isolated by distillation or by crystallisation. Additionally, the energy required in carrying out the reaction is relatively low. Thus the process according to the invention is a valuable enrichment of the art.

If p-chlorobenzotrichloride is treated at room temperature with sulphuryl chloride in the presence of a mixture of aluminum chloride and disulphur dichloride, the course of the reaction can be represented by the following equation:

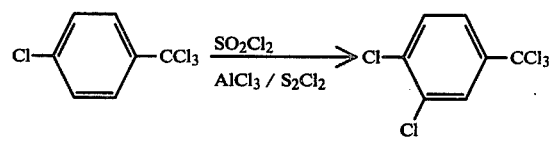

The p-chlorobenzotrichloride required as the starting material is known (see J. Amer. Chem. Soc. 57, 2066-2068 (1935)).

Both chlorine and agents which release chlorine can be used as the chlorinating agent in carrying out the process according to the invention. Agents which can be used in this procedure which release chlorine are, in particular, sulphur dichloride and sulphuryl chloride.

The reaction according to the invention is carried out in the presence of a catalyst. Suitable catalysts are iron-(III) chloride, aluminum chloride or a mixture of iron-(III) chloride or aluminum chloride and sulphur dichloride or disulphur dichloride. Aluminum chloride and disulphur dichloride and mixtures of iron(III) chloride and sulphur dichloride or disulphur dichloride are particularly preferred.

The reaction according to the invention can optionally be carried out in the presence of an inert diluent. Diluents which can be used are inert organic solvents, such as chlorinated hydrocarbons. Carbon tetrachloride may be mentioned specifically. However, the process according to the invention is preferably carried out in the absence of inert diluents.

The reaction temperatures can be varied within a wide range. In general, the reaction is carried out at a temperature between 0° C. and 180° C., preferably between 10° C. and 100° C.

In general, the process according to the invention is carried out under normal pressure. However, it can also be carried out under increased pressure, say up to 20 atm.

The reaction times can vary within a wide range. In general, they are between 30 minutes and 50 hours.

When carrying out the process according to the invention, a large excess of chlorine gas or 1 to 20 moles of an agent which releases chlorine and, in each case, 4 to 500 mmoles of catalyst or catalyst mixture are employed per mole of p-chlorobenzotrichloride. If a catalyst mixture is used, this is generally composed in such a way that it contains 0.1 to 30 mols of sulphur dichloride or disulphur dichloride per mole of iron(III) chloride or aluminum chloride, as the case may be. Those catalyst mixtures which consist of equimolar amounts of iron(III) chloride or aluminum chloride and sulphur dichloride or disulphur dichloride are preferably employed.

If the chlorination by the process according to the invention is carried out with chlorine gas, in general the procedure followed is to add the catalyst or the catalyst components to p-chlorobenzotrichloride or a solution of p-chlorobenzotrichloride in an inert diluent and to pass chlorine gas, after previously warming to the desired temperature, through this reaction mixture until at least the desired amount of chlorine has been taken up. The isolation of the reaction products is carried out by adding ice-cooled dilute hydrochloric acid to the reaction mixture after the chlorination has ended, filtering off the solid substances which precipitate, separating off the organic phase from the filtrate, drying and distilling the organic phase or, after stripping off any solvent which may be present, subjecting the remaining product to fractional crystallisation.

In a particular embodiment, the chlorination, according to the invention, with chlorine gas can also be carried out under "recycling conditions". A procedure of this type is advisable, above all, if 2,4,5- or 3,4,5-trichlorobenzotrichloride is to be prepared. The procedure followed during this chlorination under "recycling conditions" is (a) initially to pass chlorine into the above-mentioned reaction mixture over a relatively long period, (b) then to transfer the reaction mixture into a second vessel, add an ice-hydrochloric acid mixture, filter off the solid constituents, separate the organic phase from the filtrate and dry the organic phase and then (c) to distil the organic phase in a distillation apparatus so that 2,4,5,- and/or 3,4,5-trichlorobenzotrichloride are isolated separately whilst unreacted starting material and benzotrichloride which is not chlorinated highly enough are led again to the chlorination reaction in the first vessel.

DESCRIPTION OF SPECIFIC EMBODIMENT

It is to be understood that the process is applicable to the preparation of the aforementioned di- tri- or tetra-chlorobenzotrichloride compounds. Where the desired product is 3,4-dichlorobenzotrichloride the process is preferably conducted at a temperature between 20° and 90° C. for between 30 and 500 minutes. Where 3,4,5-trichlorobenzotrichloride is the desired compound the process is preferably conducted at a temperature between 20° and 60° C. for between 300 and 1.500 minutes. Similarly, when the desired product is 2,4,5-trichlorobenzotrichloride the process is preferably conducted at a temperature between 40° and 80° C. for between 100 and 1.200 minutes. When the desired compound is 2,3,4,5-tetrachlorobenzotrichloride the process is preferably conducted at the higher temperature range of 20° to 160° C. for between 100 and 500 minutes.

If the chlorination by the process according to the invention is carried out with an agent which releases chlorine, in general the procedure is to add the catalyst or the catalyst components and the agent which releases chlorine to p-chlorobenzotrichloride or a solution of p-chlorobenzotrichloride in an inert diluent, if appropriate after prior warming. The isolation of the reaction products is carried out as has already been described for the chlorination, according to the invention, with chlorine gas.

Agents which supply chlorine and are useful in accordance with the process of the invention include in particular: chlorine, sulphur dichloride and sulphuryl chloride.

In a particular embodiment, the chlorination, according to the invention, with an agent which releases chlorine can be carried out, as may the reaction with chlorine gas, under "recycling conditions". The procedure followed here is completely analogous to the procedure indicated above.

The reaction according to the invention proceeds stepwise both in the chlorination with chlorine gas and in the chlorination with an agent which releases chlorine. 3,4-Dichlorobenzotrichloride is formed first. By continuing the reaction, 3,4,5- and 2,4,5-trichlorobenzotrichloride are obtained together, higher temperatures favouring the formation of the 2,4,5-isomer. When the chlorination is continued still further, 2,3,4,5,-tetrachlorobenzotrichloride is obtained. The stepwise course of the chlorination according to the invention makes possible the controlled synthesis of particular nuclear-chlorinated benzotrichlorides. For this it is only necessary to interrupt the reaction after the desired stage is reached.

The nuclear-chlorinated benzotrichlorides which can be prepared according to the invention can be used as plasticisers for plastics or also as solvents (see German Auslegeschrift (German Published Specification)

1,269,115). Furthermore, these nuclear-chlorinated benzotrichlorides can be converted, by saponification of the trichloromethyl group, into the corresponding benzoic acids, which are suitable for the synthesis of dyestuffs (see British Patent Specification 771,416). In addition, the compounds accessible according to the invention are valuable starting materials for the preparation of substituted diphenyl ethers, which possess an outstanding herbicidal activity (see German Offenlegungsschrift (German Published Specification) 2,333,848). Thus, for example, 2,6-dichloro-4-trifluoromethyl-4'-cyanodiphenyl ether, which has the formula

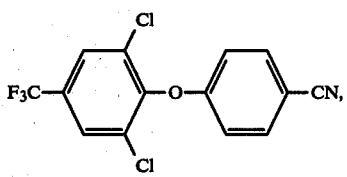

can be prepared by reacting 3,4,5-trichlorobenzotrichloride with hydrofluoric acid, under pressure, in a first stage and reacting the 3,4,5-trichlorobenzotrifluoride formed during this procedure with sodium p-cyanophenate in dimethylsulphoxide (DMSO) in a second stage.

This synthesis can be represented in terms of equations as follows:

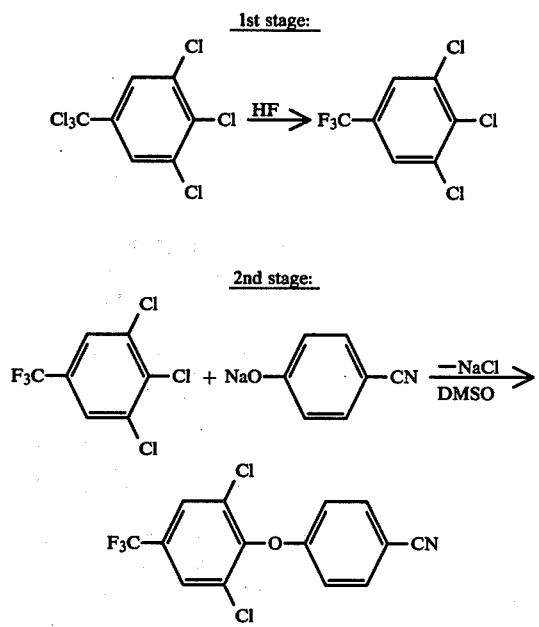

The process according to the invention is illustrated by the preparative Examples which follow.

EXAMPLE 1

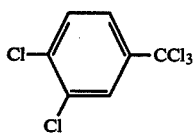

Chlorine gas was passed into a mixture of 115 g (0.5 mol) of p-chlorobenzotrichloride and 0.8 g (6 mmol) of aluminum chloride for 8.5 hours at 60° to 80° C. The mixture was then worked up by adding 200 ml of ice-cooled dilute hydrochloric acid to the reaction mixture, filtering off the solid constituents, separating off the organic phase from the filtrate, washing the organic phase five times with, in each case, 100 ml of water, then drying it over calcium chloride and subsequently distilling it over a packed column of 60 cm in length and having a silvered casing of glass. In this procedure, 100 g (75.6% of theory) of 3,4-dichlorobenzotrichloride (purity 99%) of boiling point 87° to 97° C./0.22 mm Hg were obtained. The purity and the structure of the product were unequivocally determined by a gas chromatogram and by a nuclear-magnetic resonance spectrum.

EXAMPLE 2

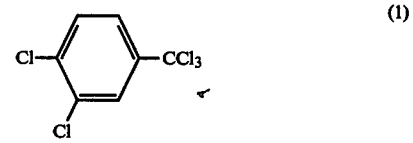

A stream of chlorine gas was passed through a mixture of 900 g (3.95 mol) of p-chlorobenzotrichloride, 3.27 g (24 mmol) of disulphur dichloride and 3.9 g (24 mmol) of iron(III) chloride for 455 minutes at 40° C. The mixture was then worked up in the manner indicated in Example 1. A product was thus obtained which consisted to the extent of 97 percent by weight of 3,4-dichlorobenzotrichloride and to the extent of 0.8% by weight of 3,4,5-trichlorobenzotrichloride. All but 0.5% of the starting material had been reacted.

EXAMPLE 3

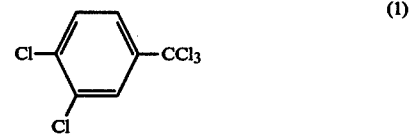

Chlorine gas was passed through a mixture of 74.4 g (550 mmol) of sulphuryl chloride, 4.6 g (34 mmol) of disulphur dichloride and 4.6 g (34 mmol) of aluminum chloride which had been added to 57.5 g (250 g mmol) of p-chlorobenzotrichloride at 20° C. The reaction mixture was stirred for 60 minutes at 20° C. and a product was obtained which consists to the extent of 97% by weight of 3,4-dichlorobenzotrichloride and, in each case, to the extent of 1.5% by weight of 3,4,5- and 2,4,5-trichlorobenzotrichloride. No further starting material could be detected in the reaction mixture by gas chromatography. For working up, ice and dilute hydrochloric acid were added to the reaction mixture and the solid constituents were filtered off. The organic phase was separated off from the filtrate, washed several times with water and, after drying, distilled in the manner indicated in Example 1.

EXAMPLE 4

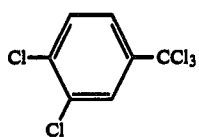 (1)

Chlorine gas was passed through a mixture of 344 g (2.55 mol) of sulphuryl chloride, 4.6 g (34 mmol) of disulphur dichloride and 4.6 g (34 mmol) of aluminum chloride which had been added dropwise to a solution of 57.5 g (250 mmol) of p-chlorobenzotrichloride in 100 ml of carbon tetrachloride at 40° C. The reaction mixture which was formed during this procedure contained, as shown by analysis by gas chromatography, 93% by weight of 3,4-dichlorobenzotrichloride, 3.3% of 2,4,5-trichlorobenzotrichloride, 3.3% of 3,4,5-trichlorobenzotrichloride and 0.4% of 2,3,4,5-tetrachlorobenzotrichloride. The isolation of 3,4-dichlorobenzotrichloride was carried out in the manner indicated in Example 1.

EXAMPLE 5

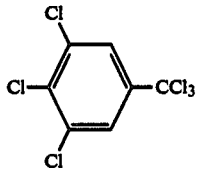 (2)

A stream of chlorine gas was passed through a mixture of 900 g (3.95 mol) of p-chlorobenzotrichloride, 3.27 g (24 mmol) of disulphur dichloride and 3.9 g (24 mmol) of iron(III) chloride for 1,400 minutes at 40° C. The product mixture which was formed during this procedure contained 60.9% by weight of 3,4-dichlorobenzotrichloride, 26.8% of 3,4,5-trichlorobenzotrichloride, 7.3% of 2,4,5-trichlorobenzotrichloride and 5.0% of 2,3,4,5-tetrachlorobenzotrichloride.

For working up, the reaction mixture was transferred into a second vessel, an ice/hydrochloric acid mixture was added there and the solid product which precipitated during this procedure was filtered off. After recrystallisation of this solid product from ethanol, 2,3,4,5-tetrachlorobenzochloride of melting point 120° C. was obtained.

The organic phase was separated off from the filtrate of the above filtration, washed several times with water and dried. Thereafter, the 3,4,-dichlorobenzotrichloride was distilled off over a packed column of 60 cm in length and having a silvered casing of glass, and this compound was then led again to the chlorination reaction in the first vessel in order to repeat the process described.

The sump mixture remaining in the above-mentioned distillation, which consisted to the extent of 79% of 3,4,5-trichlorobenzotrichloride and to the extent of 21% of 2,4,5-trichlorobenzotrichloride, was separated by distillation over a heated column of 100 cm in length which was packed with VA netting. At a reflux ratio of 1:10, a product passed over, under a head of 1.5 mm Hg at 122° C., which, according to analysis by gas chromatography and NMR spectroscopy, consisted to the extent of 99.5% of 3,4,5-trichlorobenzotrichloride. In recycling the 3,4-dichlorobenzotrichloride to renewed chlorination (recycling method), the 3,4,5-trichlorobenzotrichloride was obtained in a total yield of 68% of theory.

EXAMPLE 6

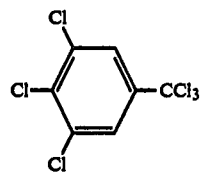 (2)

About 100 of chlorine per hour were passed into a suspension of 922 g (4.01 mol) of p-chlorobenzotrichloride, 9.22 g (56.8 mmol) of iron(III) chloride and 7.2 g (70 mmol) of sulphur dichloride for 915 minutes at 30° C. The mixture which was formed during this procedure contained 92.9% by weight of 3,4-dichlorobenzotrichloride, 5.4% of 3,4,5-trichlorobenzotrichloride and 1.5% of 2,4,5-trichlorobenzotrichloride. All but 0.2% of the starting material was consumed. The working up was carried out by the method described in Example 5, that is to say separating off, by distillation, the 3,4-dichlorobenzotrichloride and chlorinating it again. The collected sump fractions were distilled under the conditions indicated in Example 5. In this manner, 3,4,5-trichlorobenzotrichloride was obtained in a yield of 75% of theory.

EXAMPLE 7

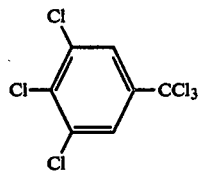 (2)

A stream of chlorine gas was passed through a mixture of 57.5 g (250 mmol) of p-chlorobenzotrichloride, 2.7 g (20 mmol) of disulphur dichloride and 3.24 g (20 mmol) of iron(III) chloride for 380 minutes at 40° C. The mixture which was formed during this procedure contained 3.6% of p-chlorobenzotrichloride, 66% of 3,4-dichlorobenzotrichloride, 20% of 3,4,5-trichlorobenzotrichloride and 6.7% of 2,4,5-trichlorobenzotrichloride. The procedure additionally followed was the "recycling method" described in Example 5, namely separating off unreacted p-chlorobenzotrichloride and 3,4-dichlorobenzotrichloride by distillation and chlorinating these substances again. After distillation of the combined sump fractions, 59% of theory of 3,4,5-trichloride were obtained.

EXAMPLE 8

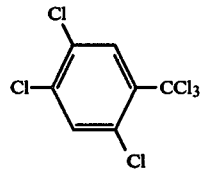 (3)

A solution of 4.6 g (34 mmol) of aluminum chloride and 4.6 g (34 mmol) of disulphur dichloride in 344 g (2.55 mol) of sulphuryl chloride was added dropwise to a mixture of 57.5 g (250 mmol) of p-chlorobenzotrichloride and 115 g (850 mmol) of sulphuryl chloride at 40° C. The reaction mixture was further processed in the manner described in Example 5, that is to say that, after the working up, unreacted p-chlorobenzotrichloride and 3,4-dichlorobenzotrichloride were separated off by distillation and fed to renewed chlorination with sulphuryl chloride under the conditions given here. By distillation of the combined sump fractions, 2,4,5-trichlorobenzotrichloride was obtained in a yield of 47% of theory.

EXAMPLE 9

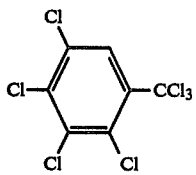

(4)

A mixture of 344 g (2.55 mol) of sulphuryl chloride, 4.6 g (34 mmol) of disulphur dichloride and 4.6 g (34 mmol) of aluminum chloride was added to a mixture of 57.5 g (250 mmol) of p-chlorobenzotrichloride and 115 g (850 mmol) of sulphuryl chloride at 22° C. and the mixture was stirred for 210 minutes. The reaction mixture which was formed contained 56% by weight of 2,3,4,5-tetrachlorobenzotrichloride, 21% of p-chlorobenzotrichloride and 3,4-dichlorobenzotrichloride and 23% of 3,4,5- and 2,4,5-trichlorobenzotrichloride. The mixture was worked up by the method described in Example 5 and, during this procedure, some of the 2,3,4,5-tetrachlorobenzotrichloride was separated off by precipitation. The rest of the 2,3,4,5-tetrachlorobenzotrichloride remained as the sump product in the distillation of the organic phase. Since the distillate contained no further by-products in addition to p-chlorobenzotrichloride, 3,4-dichlorobenzotrichloride and 2,4,5- and 3,4,5-trichlorobenzotrichloride, it was chlorinated with sulphuryl chloride again, after drying and distilling, under the abovementioned conditions. In this manner, 2,3,4,5-tetrachlorobenzotrichloride was obtained in virtually quantitative yield.

EXAMPLE 10

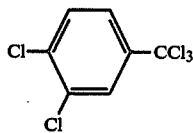

(1)

A mixture of 57.5 g (250 mmol) of p-chlorobenzotrichloride, 1.5 g (9.2 mmol) of iron(III) chloride and 28 g (272 mmol) of sulphur dichloride was warmed to 80° C. for 3 hours. Thereafter, it was worked up in the manner indicated in Example 1. 34 g of 3,4-dichlorobenzotrichloride were thus obtained.

What is claimed is:

1. A process for the preparation of 3,4-dichlorobenzotrichloride, 3,4,5-trichlorobenzotrichloride, 2,4,5-trichlorobenzotrichloride or 2,3,4,5-tetrachlorobenzotrichloride which comprises contacting at a temperature between 0° and 180° C. p-chlorobenzotrichloride of the formula

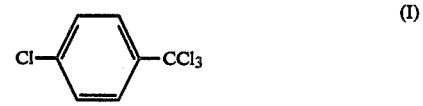

(I)

with chlorine or an agent which releases chlorine in the presence of an iron (III) chloride or aluminum chloride catalyst or a mixture of iron (III) chloride or aluminum chloride with sulfur dichloride or disulfur dichloride.

2. A process according to claim 1 wherein the reaction is carried out at a temperature between 10° and 100° C.

3. A process according to claim 1 wherein the reaction is carried out in the presence of an inert diluent.

4. A process according to claim 3 wherein the inert diluent is a chlorinated hydrocarbon.

5. A process according to claim 4 wherein the chlorinated hydrocarbon is carbon tetrachloride.

6. A process according to claim 1 wherein excess chlorine is employed relative to the amount of p-chlorobenzotrichloride.

7. A process according to claim 1 wherein the process is carried out in the presence of a mixture iron (III) chloride or aluminum chloride with sulfur dichloride or disulfur dichloride employing an agent which releases chlorine.

8. A process according to claim 1 wherein 1 to 20 mols of said agent which releases chlorine are employed per mol of p-chlorobenzotrichloride.

9. A process according to claim 1 wherein 400 to 500 mmols of iron (III) chloride or aluminum chloride or a mixture of iron (III) chloride or aluminum chloride with sulfur dichloride or disulfur dichloride are employed.

10. A process acording to claim 1 wherein a mixture of iron (III) chloride or aluminum chloride with sulfur dichloride or disulfur dichloride is employed and said mixture contains 0.1 to 30 mols of sulfur dichloride or disulfur dichloride per mol or iron (III) chloride or aluminum chloride.

11. A process according to claim 9 wherein a mixture which consists essentially an equimolar amount of iron (III) chloride or aluminum chloride and sulfur dichloride or disulfur dichloride is employed.

12. A process according to claim 1 wherein unreacted p-chlorobenzotrichloride and chlorinated benzotrichloride having less than the desired number of chlorine substituents are separated off from the reaction mixture by distillation and recycled to the chlorination process.

13. A process according to claim 1 wherein the reaction is carried out at a temperature between 20° and 90° C. for between 30 and 500 minutes whereby the reaction product comprises 3,4-dichlorobenzotrichloride.

14. A process according to claim 1 wherein the reaction is carried out at a temperature of 20° to 60° C. for between 300 and 1500 minutes whereby the reaction product comprises 3,4,5-trichlorobenzotrichloride.

* * * * *